US012575979B2

(12) United States Patent
Smith

(10) Patent No.: US 12,575,979 B2
(45) Date of Patent: Mar. 17, 2026

(54) REUSABLE ABSORBENT ARTICLE

(71) Applicant: Uma Smith, Acton, MA (US)

(72) Inventor: Uma Smith, Acton, MA (US)

( * ) Notice: Subject to any disclaimer, the term of this patent is extended or adjusted under 35 U.S.C. 154(b) by 545 days.

(21) Appl. No.: 17/924,670

(22) PCT Filed: May 10, 2021

(86) PCT No.: PCT/US2021/031599
§ 371 (c)(1),
(2) Date: Nov. 10, 2022

(87) PCT Pub. No.: WO2021/231310
PCT Pub. Date: Nov. 18, 2021

(65) Prior Publication Data
US 2023/0181388 A1      Jun. 15, 2023

Related U.S. Application Data

(60) Provisional application No. 63/117,189, filed on Nov. 23, 2020, provisional application No. 63/022,542, filed on May 10, 2020.

(51) Int. Cl.
*A61F 13/505* (2006.01)
*A61F 13/45* (2006.01)

(52) U.S. Cl.
CPC ............ *A61F 13/505* (2013.01); *A61F 13/45* (2013.01)

(58) Field of Classification Search
CPC .. A61F 13/47; A61F 13/472; A61F 13/47236; A61F 13/47245; A61F 2013/4708; A61F 2013/47281; A61F 13/5605–5616; A61F 13/505; A61F 13/45; A61F 13/49003–49006; A61F 2013/15276; A61F 13/15268; A61F 2013/5055
See application file for complete search history.

(56) References Cited

U.S. PATENT DOCUMENTS 3,970,087 A      7/1976  Castaneda
4,678,465 A  *  7/1987  Avejic ................... A61F 13/505
                                                              604/397

(Continued)

FOREIGN PATENT DOCUMENTS

KR        20150017292 A  *  2/2015  ........... A61F 13/472

OTHER PUBLICATIONS

International Search Report issued in PCT/US2021/031599 dated Oct. 29, 2021, 4 pages.

*Primary Examiner* — Susan S Su
(74) *Attorney, Agent, or Firm* — ROTHWELL, FIGG, ERNST & MANBECK, P.C.

(57) ABSTRACT

The present disclosure provides a reusable absorbent article comprising an outer shell, at least one absorbent layer within a shell interior of the outer shell, and a plurality of mechanical connectors configured to secure the reusable absorbent article to a wearable article. The outer shell can be opened to access the at least one absorbent layer in the shell interior, and the reusable absorbent article can be opened up into an inside-out configuration to allow a user to access and thoroughly clean and dry each absorbent layer and the outer shell. The present disclosure further provides an absorbent undergarment kit and a wearable article for providing absorbent relief.

20 Claims, 7 Drawing Sheets

(56)　　　　　　　References Cited

U.S. PATENT DOCUMENTS

| 4,964,859 | A | 10/1990 | Feldman |
|---|---|---|---|
| 5,807,362 | A | 9/1998 | Serbiak |
| 5,910,137 | A | 6/1999 | Clark |
| 7,763,003 | B1 | 7/2010 | Yip |
| 9,877,878 | B2 | 1/2018 | Rescorl et al. |
| 2002/0111596 | A1 | 8/2002 | Fletcher |
| 2004/0236298 | A1* | 11/2004 | Coates .................. A61F 13/476 |
| | | | 604/385.04 |
| 2009/0299313 | A1 | 12/2009 | Knightingale |
| 2012/0022485 | A1 | 1/2012 | Roe |
| 2014/0039432 | A1* | 2/2014 | Dunbar ............ A61F 13/15577 |
| | | | 604/394 |
| 2014/0114273 | A1* | 4/2014 | Sierra .................. A61F 13/665 |
| | | | 604/397 |
| 2014/0296820 | A1* | 10/2014 | Malone ............ A61F 13/49004 |
| | | | 604/385.201 |
| 2015/0080828 | A1 | 3/2015 | Suzuki |
| 2016/0143789 | A1 | 5/2016 | Bryan |

* cited by examiner

FIG. 6

REUSABLE ABSORBENT ARTICLE

This application is a 35 U.S.C. 371 National Phase Entry Application from PCT/US2021/031599 filed May 10, 2021, which claims priority to and the benefit of U.S. Provisional Patent Application Nos. 63/022,542, filed on May 10, 2020 and 63/117,189 filed Nov. 23, 2020, the disclosures of which are incorporated herein by reference in their entirety.

FIELD OF THE DISCLOSURE

This disclosure relates to a reusable absorbent article configured to receive bodily excrement.

BACKGROUND

Many people experience unwanted bodily discharge at some point during their lives. For some people, unwanted discharge is a recurrent challenge. For example, people face the challenge of managing bodily discharge, such as urine, feces, blood, discharge, and afterbirth. Some people experience natural daily discharge or monthly menses. Other individuals suffer from ailments including leaky bladder/incontinence, irritable bowel syndrome, loose bowels, diarrhea, among other bodily discharge challenges. These individuals often face life-long issues with finding products to catch the bodily discharge that have high enough absorbency, avoid leakage and spillage of the discharge, and maintaining sanitation/hygiene. For instance, even with conventional absorbent products (e.g., diapers, panty-liners, menstrual products), bodily fluids may still spill over and leak onto the user's undergarments. During everyday use and through natural movement, the absorbent products often become unsecured and move from their position against the user's groin, allowing the excreted fluid to soil and stain surrounding clothing. Furthermore, changing and cleaning the absorbent products is often messy, unsanitary, and toxic, especially when the user must physically touch the liquid/discharge due to poor hygiene or lack of adequate absorbent products. This is a particular concern for individuals in those areas of the world without running water. People living in areas of poverty also often lack proper waste management systems and trash disposal, making single-use, disposal products a cost-prohibitive and wasteful option. For many individuals, frequent trips to the restroom, managing soiled and foul-smelling clothing, and even purchasing products that provide absorbent relief often create a stigma of shame and embarrassment within the community.

Menstruation, in particular, presents a unique array of challenges. In many, cultures, women and girls are isolated during menses or are otherwise disgraced or shamed by the community. Due to social stigmas and lack of proper menstrual care, menstruation is one of the main reasons that girls stay home from school, with about 10% of girls in Sub-Saharan Africa and about 25% of girls in India missing school on their periods.

In many areas of the world where penetration before marriage is considered a sin, women are limited to just external protection (e.g., menstrual pads, liners, or sanitary napkins), as opposed to tampons, cups, insertable discs, or the like. Single-use, disposable menstrual pads are often cost-prohibitive and wasteful, and are not a feasible option in areas with limited waste management. While reusable menstrual pads have increased attendance to some degree, a lack of privacy and sanitary conditions for changing and cleaning pads at school still keeps many girls home. Only 41% of school bathrooms in India and Africa are girls-only, and many school bathrooms do not have running water, preventing girls from being able to rinse the reusable pads and wash their hands. Without the means and sanitary conditions to clean the pads at school, girls are forced to place used pads in a bag until they return home to wash them. However, carrying a bag to the restroom is an Obvious sign of menses and is an added source of embarrassment.

Reusable menstrual pads are often washed and dried in hiding. Washing current market-available reusable pads requires using enough water to penetrate multiple layers of fabric, wasting water, which is a valuable resource. The multi-layered design also requires lengthy drying times, in some instances, more than 24 hours. Furthermore, with multiple layers that do not come apart, it is also difficult to determine whether all layers have been sufficiently cleaned and dried. With insufficient cleaning and drying times, pads are often still wet the next morning, leading girls to wear damp or unsanitary pads to school. This creates a breeding ground for bacteria, which can lead to the development of bacterial infections.

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

In one embodiment, the present disclosure provides a reusable absorbent article, including a housing, an absorbent body, an enclosing mechanism, and at least one first mechanical connector. The housing includes a first pair of wings and a middle portion between the first pair of wings. The absorbent body includes a plurality of portions, wherein the portions are connected to each other and the absorbent body is foldable to produce a stacked configuration of the plurality of portions. The enclosing mechanism is configured to enclose the absorbent body within the housing in a pouch configuration. The at least one first mechanical connector is affixed to the housing and configured to secure the first pair of wings over a pouch opening when the absorbent body is enclosed in the pouch configuration. The reusable absorbent article includes a housed configuration and an unhoused configuration. The housed configuration comprises the absorbent body secured to the housing. The unhoused configuration comprises the absorbent body unsecured to the housing and the absorbent body in an unstacked state. The unstacked state is configured to allow passage of air over a surface area of each of the plurality of portions.

In some examples, the housing further includes a second pair of wings. The first pair of wings extends from longitudinal sides of the middle portion and the second pair of wings extends from latitudinal sides of the middle portion. In some examples, a first latitudinal wing and a second latitudinal wing each include a pocketed portion configured to receive end portions of the absorbent body.

In some examples, the at least one first mechanical connector comprises a first clasp on a medial side of a first longitudinal wing and a second clasp on a lateral side of a second longitudinal wing. In some examples, in the pouch configuration i) the first longitudinal wing folds over a portion of the absorbent body, ii) the second longitudinal wing folds over a portion of the absorbent body and a portion of the second longitudinal wing, and iii) the first clasp couples to the second clasp.

In some examples, a width of the first set of wings is at least as long as a width of the absorbent body in the stacked configuration.

In some examples, the housing further includes at least one second mechanical connector and the absorbent body further includes at least one third mechanical connector. The at least one second mechanical connector couples to the at least one third mechanical connector when the reusable absorbent article is in the housed configuration.

In some examples, each portion of the plurality of portions further includes at least one fourth mechanical connector configured to couple to a corresponding mechanical connector on an adjacent portion and secure the plurality of portions in the stacked configuration.

In some examples, any of the at least one first mechanical connector, the at least one second mechanical connector, the at least one third mechanical connector, and the at least one fourth mechanical connector comprises any of: hook-and-loop fasteners, male and female connectors, zippers, lip and tape fasteners, double track fasteners, rivets and eyelets, cufflinks, buttons, snaps, clasps, eyelets and laces, or safety pins.

In some examples, each portion of the plurality of portions comprises a material with high absorbency and configured to inhibit bacterial growth. In some examples, each portion of the plurality of portions comprises different levels of absorbency.

In some examples, the enclosing mechanism includes a drawstring. For example, the drawstring comprises at least one tab. For example, the drawstring comprises a first tab at a first latitudinal wing portion and a second tab at a second latitudinal wing portion.

In some examples, the housing further comprises a plurality of flaps on a lateral side of the housing. For example, the plurality of flaps are configured to receive the absorbent body between the plurality of flaps and a middle portion of the housing. For example, the plurality of flaps completely enclose the absorbent body when the absorbent body is received by the plurality of flaps. In some examples, the absorbent body is configured to hold up to 12 times its weight in liquid.

In some examples, the housing comprises a waterproof material.

In some examples, the plurality of portions comprises a first portion configured to inhibit bacterial growth and one or more portions configured to have high absorbency.

In some embodiments, the present disclosure provides a reusable absorbent article comprising an outer shell (or housing), wherein the outer shell comprises a front panel coupled to a back panel, wherein a shell interior is formed between the front and back panels. A plurality of absorbent layers are positioned within the shell interior and are secured between the front and back panels. The plurality of absorbent layers are also cut along a length to allow for separation of the absorbent layers. The back panel of the outer shell comprises a first flap that at least partially overlaps with a second flap which can be opened to access the plurality of absorbent layers. At least one mechanical connector is configured to secure the reusable absorbent article to a wearable article, and the reusable absorbent article comprises a closed configuration, a partially open configuration, and an inside-out configuration. The reusable absorbent article can be opened up into an inside-out configuration to allow a user to access and thoroughly clean each of the plurality of absorbent layers and the front and back panels of the outer shell.

In some embodiments, the present disclosure provides a reusable absorbent article comprising an outer shell (or housing), wherein the outer shell comprises a front panel coupled to a back panel, wherein a shell interior is formed between the front and back panels. At least one absorbent layer is positioned within the shell interior and is secured between the front and back panels. The front panel of the outer shell, configured to be worn against the groin of a user, comprises a first flap that at least partially overlaps with a second flap which can be opened to access the at least one absorbent layer. The front panel further comprises a pair of wings, and at least one of the pair of wings comprises at least one mechanical connector configured to secure the reusable absorbent article to a wearable article. The back panel comprises at least one fastener (e.g., a hook and loop fastener) configured to secure the reusable absorbent article to a wearable article. The reusable absorbent article comprises a closed configuration, a partially open configuration, and a fully open configuration. The reusable absorbent article can be opened up into an inside-out configuration to allow a user to access and thoroughly clean each absorbent layer and the front and back panels of the outer shell.

In some embodiments, the present disclosure provides an absorbent undergarment kit comprising at least one reusable absorbent article, a wearable article, and a plurality of mechanical connectors configured to secure the reusable absorbent article to the wearable article. In some examples, the wearable article comprises a band for securing an end portion of a reusable absorbent article while allowing for vertical flexibility and movement of the reusable absorbent article to accommodate the user's movement.

In some embodiments, the present disclosure provides a wearable article for providing absorbent relief comprising an undergarment, a reusable absorbent article, and at least one attachment mechanism securing the reusable absorbent article to the undergarment.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

FIG. 6 shows an exemplary fully opened configuration of a reusable absorbent article, according to an embodiment of the present disclosure.

DETAILED DESCRIPTION

Figure 1:
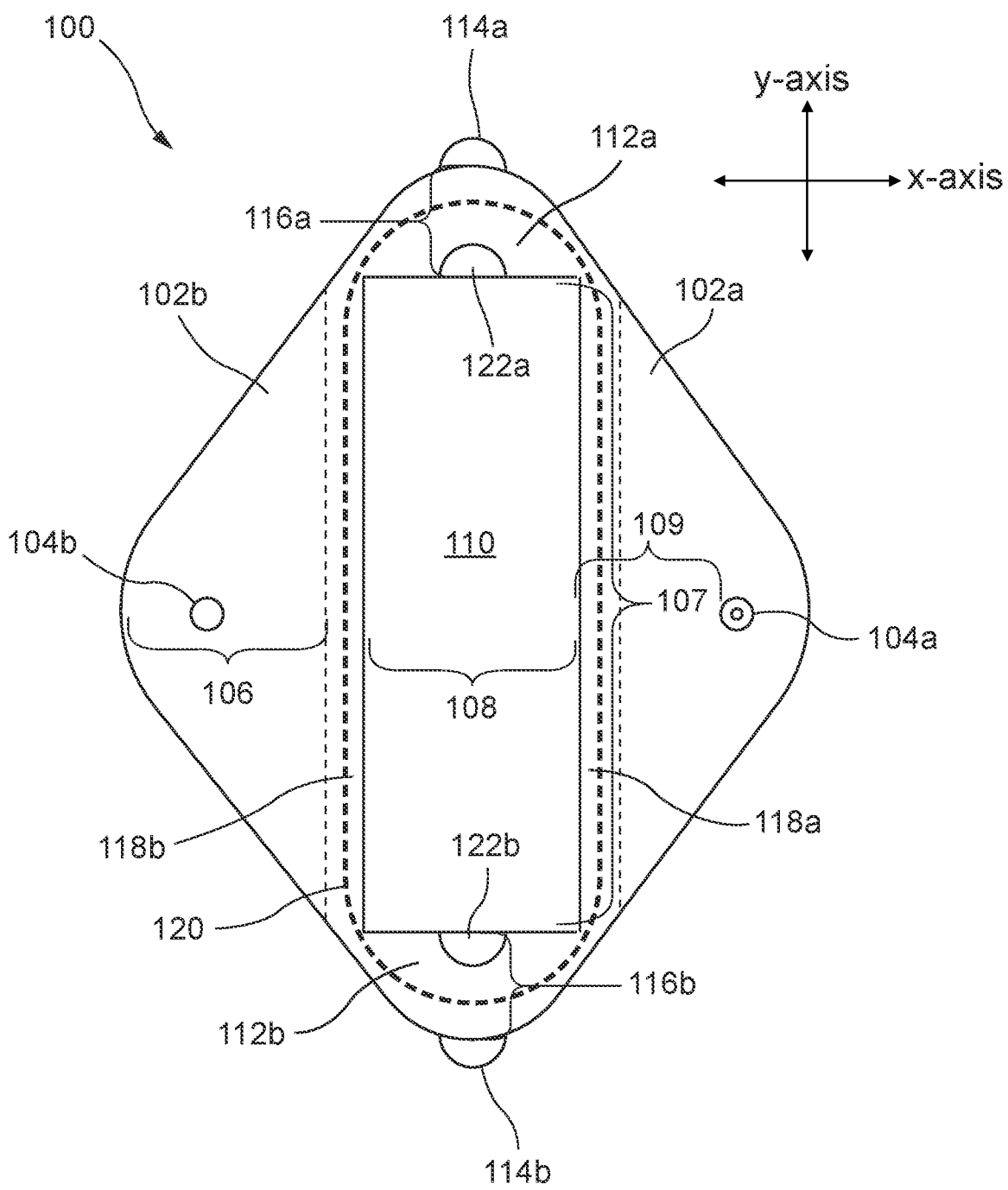
FIG. 1 shows a medial view of an exemplary reusable absorbent article housing, according to an embodiment of the present disclosure.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of right of, in front of, behind, next to, adjacent, between, horizontal, vertical, diagonal, longitudinal, transverse, radial, axial, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the disclosure and are not intended to be limiting.

To the extent used herein, the term "adjacent" refers to being near or adjoining. Adjacent objects can be spaced apart from one another or can be in actual or direct contact with one another. In some instances, adjacent Objects can be coupled to one another or can be formed integrally with one another.

To the extent used herein, the terms "substantially" and "substantial" refer to a considerable degree or extent. When used in conjunction with, for example, an event, circumstance, characteristic, or property, the terms can refer to instances in which the event, circumstance, characteristic, or property occurs precisely as well as instances in which the event, circumstance, characteristic, or property occurs to a close approximation, such as accounting for typical tolerance levels or variability of the embodiments described herein.

To the extent used herein, the terms "optional" and "optionally" mean that the subsequently described, component, structure, element, event, circumstance, characteristic, property, etc. may or may not be included or occur and that the description includes instances where the component, structure, element, event, circumstance, characteristic, property, etc. is included or occurs and instances in which it is not or does not.

To the extend used herein, the term "mechanical connector" refers to any of: hook-and-loop fasteners, male and female connectors, zippers, lip and tape fasteners, double track fasteners, rivets and eyelets, cufflinks, buttons, snaps, clasps, eyelets and laces, one or more adhesives, safety pins, or silicone ridges.

The present disclosure provides a reusable absorbent article which comprises a waterproof shell or housing and an absorbent body that may be secured within the waterproof housing. The reusable absorbent article is securable to the user's undergarments or other clothing, and prevents the bodily discharge from leaking from the absorbent body and spilling onto the user's undergarments or other clothing. The absorbent body is foldable or stacked and comprises a plurality of portions, wherein the portions are connected to each other and the absorbent body is made of stacked layers or foldable to produce a stacked configuration of the plurality of portions. This stacked configuration allows for multi-layered absorbency and leak protection, and can hold up to 12 times its weight in liquid until it becomes saturated. This absorbency reduces the need to replace the article. When the absorbent body is unfolded into a single layer or opened to separate the layers, it can be washed thoroughly (with less water than conventional products) and dried quickly to reduce bacterial growth. At least one of the portions of the plurality of portions may comprise an antibacterial material to further prevent infection.

The reusable absorbent article may further comprise a drawstring, or another mechanical mechanism, configured to secure the absorbent body within the housing in a pouch configuration. This pouch configuration allows for any messy or toxic liquid/excrement to be contained, without the need for the user to physically touch the absorbent body or housing, which may be contaminated. This feature is particularly advantageous for users who must remove an absorbent body from their clothing without access to running water to wash their hands afterwards. The pouch configuration also creates a discreet and hygienic solution for carrying the used absorbent article home for cleaning, and can be secured with the drawstrings underneath the user's skirt or clothing. It also eliminates the need to bring an extra bag to the bathroom and allows for a fast-changing process. Ultimately, the pouch may be used to increase school attendance for girls on their period and to reduce menstrual taboos.

FIG. 1 shows a medial view of an exemplary reusable absorbent article housing 100, according to an embodiment of the present disclosure. Housing 100 includes longitudinal wings 102a, 102b; mechanical connectors 104a, 104b; middle portion 110; latitudinal wings 112a, 112b, tabs 114a, 110; pocketed portions 116a, 116b, lip portions 118a, 118b; drawstring 120; and pull indicators 122a, 122b.

Housing 100 is made of a waterproof material, configured to prevent liquid from passing through the housing, from a medial side as shown in FIG. 1 to a lateral side (not shown). Exemplary waterproof materials include, but are not limited to, any of: nylon, rip-stop, polyurethane laminate, latex, natural rubber, thermoplastic polyurethane, laminated fabrics (such as laminated cotton and poplin), oilcloth, polyester fleece, fabrics with a waterproof or water resistant coating laminate, wool, vinyl, pleather, plastic, densely woven branded fabrics (such as Ventile), and synthetic waterproof or water resistant fabrics (such as Gore-Tex). In some instances, the waterproof or water resisting coating/ laminate comprises a waterproofing material such as rubber, polyvinyl chloride, polyurethane, silicone elastomer, fluropolymers, and/or wax. Pull indicators 122a, 122b may also comprise a waterproof material, and may be a different color than the rest of the housing 100 to indicate where the user should pull when opening up the reusable absorbent article (e.g., from the pouch configuration). In some examples, a middle portion 110 is made of a non-waterproof material. The middle portion 110 has a longer length 107 than width 108. For example, the length 107 and the width 108 of the middle portion 110 are configured to be approximately the size of a groin portion of a user's underwear. In some examples, the length 107 and the width 108 of the middle portion 110 vary according to a preference and/or size of the user. In some examples, the housing 100 is square-shaped instead of diamond shaped, but the shape of the housing 100 is not limited for purposes of this disclosure.

Housing 100 includes a plurality of wings 102a, 102b, 112a, 112b along edges of the middle portion 110. For example, wings 102a and 102b are a first set of wings extending along longitudinal sides (e.g., along a y-axis) of the middle portion 110, and wings 112a and 112b are a second set of wings extending along latitudinal sides (e.g., along an x-axis) of the middle portion 110. Longitudinal wings 102a, 102b include mechanical connectors 104a and 104b, which are configured to couple to each other. In some examples, a width 106 of longitudinal wings 102a, 102b is less than a width 108 of the middle portion 110. In some examples, a distance from an edge of the middle portion 110 to each of the mechanical connectors 104a, 104b (shown as distance 109 to mechanical connector 104a) is approximately equal to half of the distance of width 108. Accordingly, in some configurations (not shown), mechanical connectors 104a, 104b secure the housing 100 around the groin section of underwear.

Latitudinal wings 112a and 112b respectively include pocketed portions 116a, 116b. For example, pocketed portions 116a, 116b are fabric flaps with an opening facing the middle portion 110.

Housing 100 further includes a drawstring 120 extending around a perimeter of the middle portion 110 and the latitudinal wings 112a, 112b. For example, the drawstring 120 is completely enclosed within the housing 100 except for tabs 114a, 114b adjacent to tip portions of the latitudinal wings 112a, 112b. When the drawstring 120 is pulled at tabs 114a, 114b; the housing 100 collapses into a pouch configuration (discussed further below regarding FIG. 3). In some examples, the drawstring 120 is made of a stretchy and/or elastic material. In some examples, the drawstring 120 is a string having minimal elasticity. An exemplary material for the drawstring 120 includes spun polyester. In some examples, the tabs 114a, 114b are made of plastic or cloth. In other examples, housing 100 does not include tabs 114a, 114b, and the user pulls directly on the drawstring 120 to collapse the housing 100.

In some embodiments, drawstring 120 is one or more mechanical connectors along the shown perimeter of the middle portion 110 and the latitudinal wings 114a, 114b. For example, drawstring 120 is a zipper that can be used to seal the housing 100 along a longitudinal y-axis. In some embodiments, the housing 100 does not include a drawstring, and instead includes an alternative folding or collapsing mechanism to enclose and secure the absorbent body within the housing 100.

Housing 100 also includes lip portions 118a, 118b. For example, lip portions 118a, 118b are narrow sections of fabric extending over the middle portion 110. In some examples, lip portions 118a, 118b are open along edges of the middle portion 110 and sealed shut along edges of the longitudinal wings 102a, 102b. Therefore, the lip portions 118a, 118b provide spill and leak protection for liquid received in the middle portion 110. For example, when the housing 100 is worn by a user and receives bodily fluids, the fluid does not leak onto the user's undergarments, because the liquid is caught by the lip portions 118a, 118b and the pocketed portions 116a, 116b. In some embodiments of the present disclosure, housing 100 does not include lip portions 118a, 118b or pocketed portions 116a, 116b.

Figure 2:
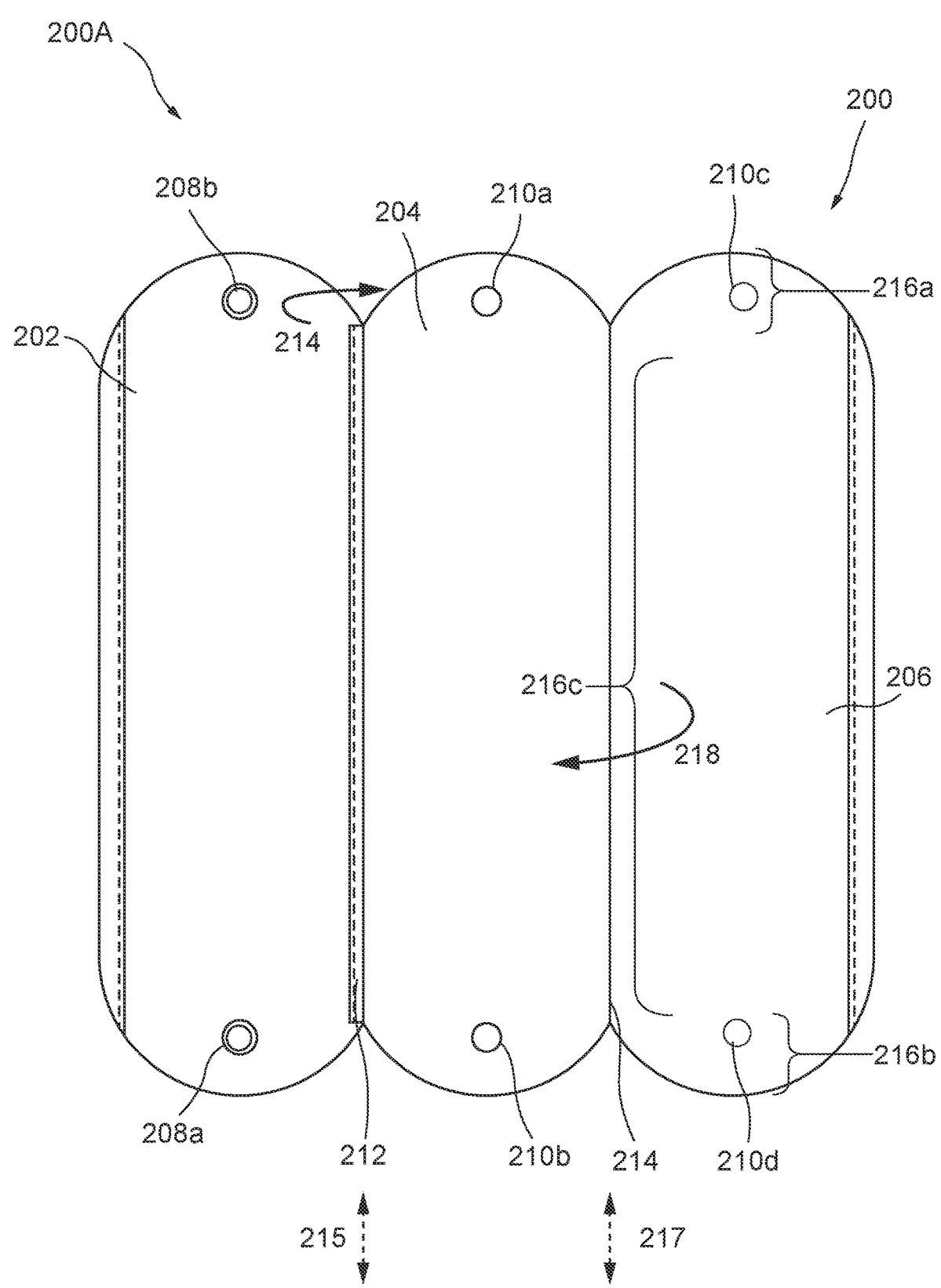
FIG. 2 shows an exemplary unstacked, or unfolded, configuration of an absorbent body, according to an embodiment of the present disclosure.

FIG. 2 shows an exemplary unstacked configuration 200A of an absorbent body 200, according to an embodiment of the present disclosure. An exemplary absorbent body 200 includes a plurality of portions 202, 204, 206; at least one mechanical connector 208a, 208b; a plurality of openings 210a, 210b, 210c, 210d; and crease portions 212, 214. Although FIG. 2 shows an absorbent body 200 with three exemplary portions 202, 204, 206, the present disclosure contemplates that absorbent body 200 can include any number of portions as long as there is at least one portion. In an alternative embodiment, the plurality of portions are attached to each other along one edge such that the portions can be separated at the open edge but not unfolded. In still another embodiment, the plurality of portions are attached along two opposite edges with a cut in the plurality of portions to allow the layers to be separated.

Portions 202, 204, and 206 comprise materials with high absorbency and/or materials configured to inhibit bacterial growth. In some examples, each portion 202, 204, and 206 has different absorbencies. For example, portions 204 and 206 have higher absorbencies than portion 202. In some examples, the absorbent body 200 is configured to hold up to 12 times its weight in liquid. In some examples, portion 202 comprise materials primarily configured to inhibit bacterial growth, and portions 204, 206 comprise materials primarily configured to provide high absorbency levels for the absorbent body 200. Exemplary high absorbency materials include, but are not limited to, one or more of: cotton, cotton blends, polar fleece, nylon, terry fabrics (such as cotton terry and hemp terry), Flannelette, bamboo including bamboo fleece, bamboo charcoal fabric, and bamboo blends such as thermoplastic polyurethane/bamboo charcoal fabric blends, microfiber, Zorb® superabsorbent fabrics (non-woven, tangled cellulose fiber fabric), hemp, hemp blends, Turkish cotton velour, wool, linen, rayon, hydrophilic non-woven fabric. Exemplary materials configured to inhibit bacterial growth include one or more of: antimicrobial fabrics containing copper alloys, antimicrobial fabrics containing silver alloys or silver ions, fabrics with organosilane coatings, fabrics containing bactericides (such as antibiotic coatings), fabrics containing viral inhibitors, fabrics containing fungal inhibitors, fabrics with antimicrobial additives (e.g. biocides such as triclosan), fabrics with self-cleaning coatings (such as photocatalytic coatings), hemp, bamboo, and linen. In some examples, any polyester materials are recyclable and any natural materials (e.g., the charcoal bamboo material or hemp materials) can be composted at the end of the lifecycle of the reusable absorbent article.

Each portion 202, 204, 206 includes a first end segment, a second end segment, and a body segment (shown as 216a, 216b, and 216c respectively regarding portion 206).

Absorbent body 200 further includes mechanical connectors 208a, 208b. In some examples, mechanical connectors 208a, 208b are housed on first and second end portions of a first portion 202, and second portion 204 and third portion 206 include openings 210a, 210b, 210c, 210d positioned corresponding to positions of mechanical connectors 208a, 208b. Accordingly, when absorbent body 200 is in a stacked configuration, mechanical connector 208a is aligned with openings 210a, 210c, and mechanical connector 208b is aligned with openings 210b, 210d. Accordingly, mechanical connectors 208a, 208b configure the absorbent body 200 to couple with another apparatus, including, for example, housing 100.

Portions 202 and 204 are connected by crease portion 212, and portions 204 and 206 are connected by crease portion 214. In some examples, crease portions 212, 214 are seams. In other examples, crease portions 212, 214 are sections of fabric configured to fold such that portions 202, 204, and 206 are adjacent to each other. For example, crease portion 212 configures portion 202 to rotate clockwise 214 about a vertical axis 215 (e.g., into the page from the viewer's perspective) such that portion 202 is directly adjacent to portion 204. For example, crease portion 214 configures portion 206 to rotate clockwise 218 about a vertical axis 217 (e.g., out of the page from the viewer's perspective). Therefore, absorbent body 200 is configured to fold in a zig-zag configuration. In other examples, portions 202 and 206 are rotatable in either a clockwise or counterclockwise direction. In some examples, crease portion 212 has a greater width than crease portion 214.

Therefore, absorbent body 200 is configured to unfold into an unstacked configuration 200A to provide airflow over an entire surface area of each of the portions 202, 204, 206. This provides quick drying and reduces the possibility of moisture being trapped between the portions 202, 204, 206, Trapped moisture promotes bacterial growth. The unstacked configuration 200A inhibits the growth of bacteria by promoting complete drying of portions 202, 204, 206.

Absorbent body 200 may be stacked such that portions 202, 204, and 206 are aligned adjacent to each other. For instance, a frontal view of the stacked configuration (not shown) of absorbent body 200 would include a frontal view of portion 202, where portions 204, 206 are behind or underneath portion 202. The stacked configuration of the absorbent body 200 has high absorbency properties. For example, each of portions 202, 204, and 206 can receive and absorb liquid. If portion 202 is unable to absorb the full amount of liquid that the absorbent body 200 is exposed to, the liquid can be absorbed by portion 204, which is behind or underneath portion 202. If portion 204 is unable to absorb the full amount of liquid that portion 204 receives, portion 206 can absorb the remaining liquid.

An exemplary reusable absorbent article, according to one embodiment of the present disclosure, includes the absorbent body 200 of FIG. 2 secured in the housing 100 of FIG. 1. For example, FIGS. 1-2 show the absorbent body 200 unhoused from the housing 100.

The pocketed portions of the latitudinal wings of the housing 100 are configured to receive the end segments of the absorbent body 200, when the absorbent body 200 is in a stacked configuration. For example, a width of the latitudinal wings is substantially similar to a width of the absorbent body 200 in the stacked configuration 200. For example, a length of the absorbent body 200 is substantially similar to a length of the housing 100. The longitudinal edges of the absorbent body 200 are received under lip portions 118a, 118b of the housing 100. Accordingly, the reusable absorbent article provides waterproofing, spill protection, and/or leak protection from liquid received by absorbent body 200 because any liquid not absorbed by the absorbent body 200 is restricted from exiting the housing 100.

In some examples, the absorbent body 200 is secured to the housing 100 in the stacked configuration 200 by mechanical connectors. For example, the housing 100 comprises at least one mechanical connector on the middle portion (not shown), and the absorbent body comprises at least one mechanical connector (e.g., mechanical connectors 208a, 208h) configured to couple to the at least one mechanical connector on the middle portion.

The reusable absorbent article, comprising the absorbent body 200 secured within the housing 100 is configured to be placed in a user's undergarments. For example, the article can be placed in underwear, briefs, thongs, boxers, or directly on a user's pants, trousers, or shorts. Absorbent body 200 is configured to be adjacent to a user's groin. In some examples, longitudinal flaps of the housing 100 secure the article onto a user's undergarments. Therefore, absorbent body 200 can receive bodily discharge from the user, including urine, feces, menstrual blood, discharge, blood, or any other excrement. The waterproof housing 100 prevents the bodily, discharge from leaking from the absorbent body 200 onto the user's undergarments or other clothing. Accordingly, the article is configured to provide absorbent relief in a variety of situations. Exemplary situations include menstrual bleeding, daily discharge, leaky bladder, irritable bowel syndrome, loose bowels, and diarrhea.

FIG. 1-2 also demonstrate the reusable nature of the disclosed article and its various embodiments and components. For example, the absorbent body 200 can be configured as a stack, affixed to the housing 100, and worn by a user. When the user is finished (e.g., the absorbent body has reached its absorbency maximum and/or the article is dirty, contaminated, and/or smelling), the user can easily uncouple the absorbent body 200 from the housing 100 and unstack the plurality of portions 202, 204, 206 in order to clean the article. Thus, whereas conventional reusable menstrual products typically take more than 24 hours to dry, in some embodiments of the present disclosure, the reusable absorbent article dries in approximately four hours. For example, users have difficulty identifying if conventional reusable products are dried, whereas a user can readily identify whether an embodiment of the present disclosure is dry due to the opening and separation of the layers. Users have trouble cleaning the various layers of conventional reusable products, but the foldable or stacked design of the disclosed reusable absorbent article provides an easily cleanable product.

Figure 3:
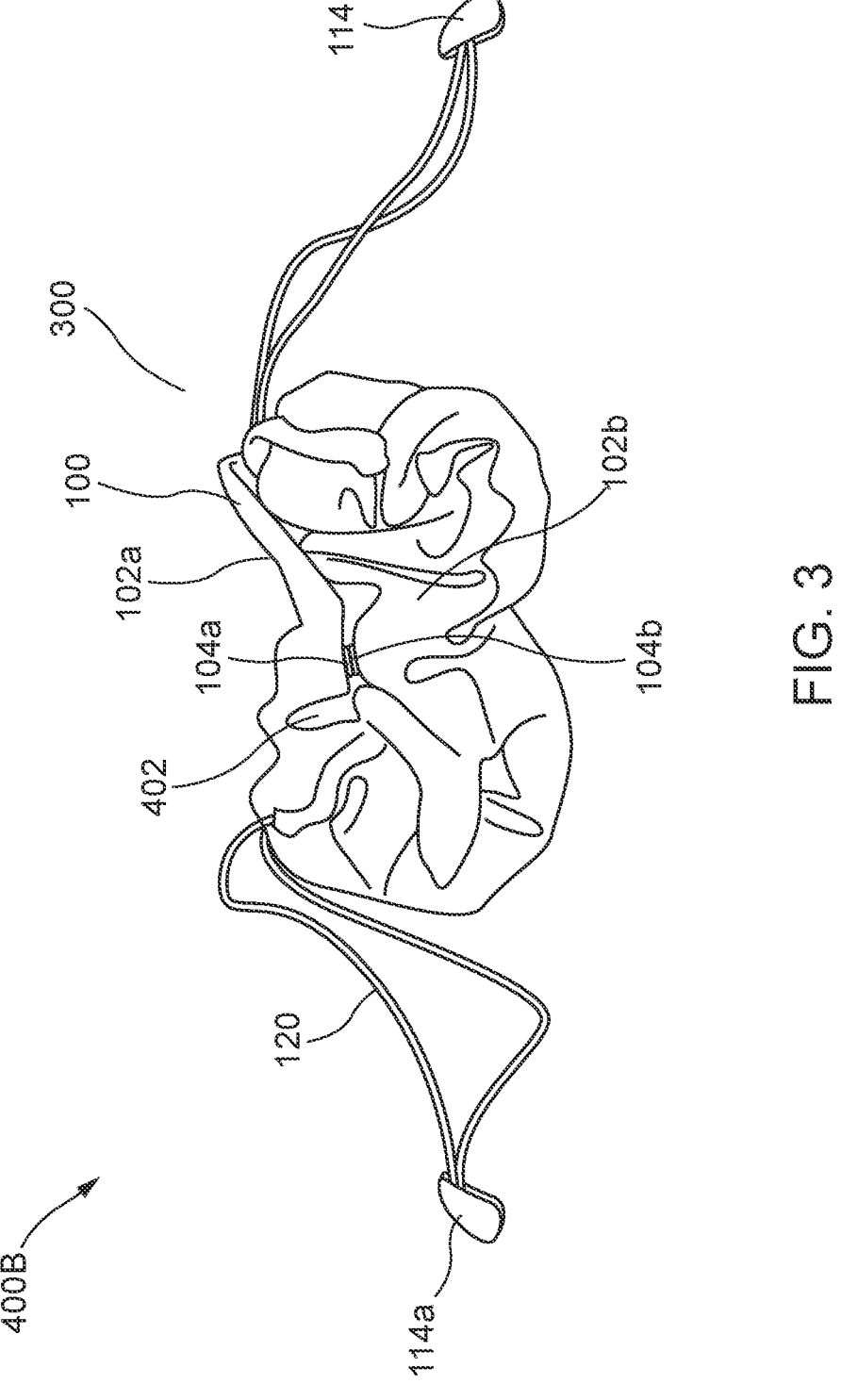
FIG. 3 shows an exemplary configuration as a drawstring is pulled to enclose an absorbent body within a housing, according to an embodiment of the present disclosure.

The reusable absorbent article may be configured to move progressively from an open configuration to a fully-enclosed pouch configuration (as shown in FIG. 3). For example, a user completes this progression by pulling a drawstring 120 to enclose a stacked absorbent body 200 within a housing 100, according to an embodiment of the present disclosure. As the user begins to pull on the drawstrings 120, the stacked absorbent body 200 is caused to compress but is still accessible via an opening 402.

FIG. 3 shows an exemplary configuration 400B where mechanical connectors 104a, 104b are coupled to each other. For example, a first longitudinal wing 102a folds over a portion of the absorbent body 200, a second longitudinal wing 102b folds a portion of the absorbent body 200 and a portion of the first longitudinal wing 102a, and the mechanical connectors 104a, 104b couple to each other. For example, a coupling portion of mechanical connector 104a is on a medial side of the first longitudinal wing 102a, and a coupling portion of mechanical connector 104b is on a lateral side of the second longitudinal wing 102b, In some non-limiting examples, mechanical connectors 104a, 104b are clasps, snaps, and/or male and female connectors, Therefore, mechanical connectors 104a, 104b are configured to secure the longitudinal wings 102a, 102b over a pouch opening 402 when the absorbent body 200 is enclosed in a pouch configuration. Configuration 400B substantially reduces opening 402 and the corresponding accessibility of absorbent body 200, The ends of the drawstring 120 may be tied together to further enclose the absorbent body 200 within the housing 100, providing additional restrictions on liquid or excrement contained in the absorbent body 200 from exiting the housing 100. The drawstring 120 may be used to secure the reusable absorbent article under a user's skirt for privacy and discretion. This is in contrast to conventional reusable products which are carried by hand and can be a source of embarrassment.

The progressive change of the reusable absorbent article from the open configuration to the fully-enclosed pouch configuration further demonstrates the sanitary nature of the disclosed article. In some examples, the liquid/excrement retained by the article is toxic, a contaminant, and/or messy. A user may wish to avoid contact with the liquid/excrement while securing the article in a pouch configuration. Accordingly, the progressive change in configurations allows the user to put the article in a pouch configuration without physically touching the absorbent article 200, without physically touching liquid/excrement contained by the absorbent article 200, and/or without physically touching portions of the housing 100, which may be contaminated. This feature is particularly advantageous for users who must remove article from their clothing without access to running water to clean their hands afterwards.

Figure 4:
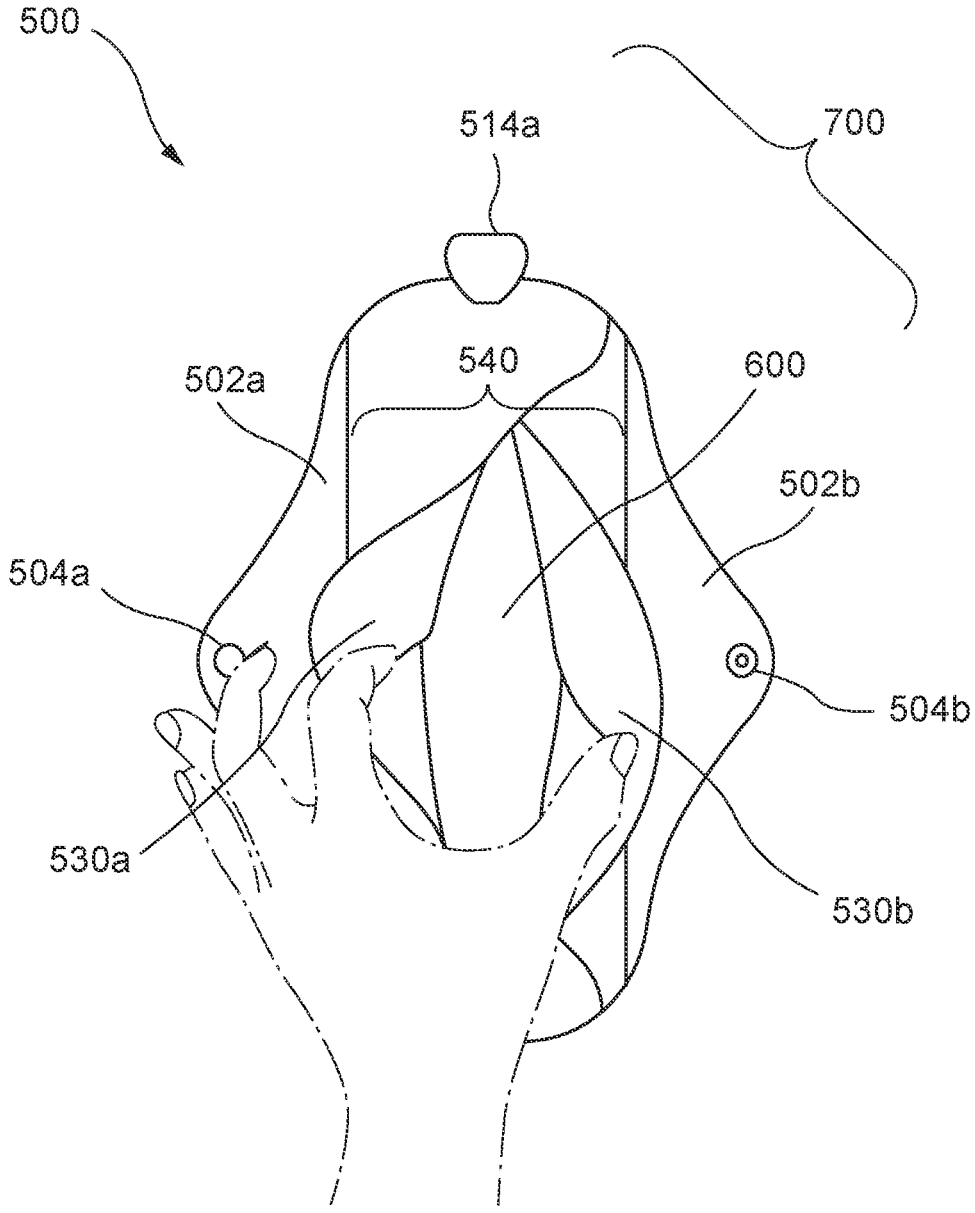
FIG. 4 shows an absorbent body secured within a housing, according to an embodiment of the present disclosure.

FIG. 4 shows a lateral view of a user accessing an interior compartment of housing 500 of a reusable absorbent article 700, according to an embodiment of the present disclosure. Housing 500 includes many similar features and labels as housing 100 of FIG. 1. For example, longitudinal wings 502a, 502b can be as described with respect to the descriptions of longitudinal wings 102a, 102b above, Housing 500 additionally includes a plurality of flaps 530a, 530b; an interior compartment 540; and lining (not shown) on a medial side of the housing 500. Altogether, the reusable absorbent article 700 shown in FIG. 4 provides similar advantages to the reusable absorbent article described above with respect to FIGS. 1-2. Additional features of housing 500 and article 700 are discussed further below.

The lining (not shown) on the medial side of housing 500 is received adjacent to a user's groin. For example, the lining is made of the same material as the material described above regarding portions 202, 204, 206 of FIG. 2. In some embodiments, the lining comprises a material configured to inhibit bacterial growth, such as those discussed above with regard to portions 202, 204, 206 of FIG. 2.

A lateral side of the housing 500 includes a plurality of flaps 530a, 530b. For example, flap 530a is configured to overlap flap 530b. As shown in FIG. 4, the housing 500 is configured to receive one or more of an absorbent body 600 at an interior compartment 540, beneath the flaps 530a, 530b (e.g., the absorbent body 600 can be as described above regarding absorbent body 200 of FIG. 2, and the absorbent body 600 is described further below regarding FIG. 6). In some examples, the overlapping nature of flaps 530a, 530b reduces liquid or excrement leakage from the interior compartment 540 onto a user's undergarments and/or clothing. In some examples, flaps 530a, 530b are mostly, but not entirely waterproof to prevent leakage from a medial side (not shown) of the housing 500 to a lateral side of the housing 500. In some examples, flaps 530a. 530b are coupled and/or sealed by mechanical connectors (not shown).

Therefore, housing 500, as shown in FIG. 4, provides unique advantages in the amount of absorbent bodies 600 that a user may place within the interior compartment 540. For example, if a user is having minimal menstrual bleeding or other excrement leakage, the user can wear just the housing 500, with the lining (not shown) on the medial side of the housing 500 worn adjacent to the groin, without an absorbent body 600, In some examples, such a configuration is more comfortable for a user. On the other hand, if a user is having a great amount of menstrual bleeding or other excrement leakage, the interior compartment 540 is configured to receive more than one absorbent body 600. Accordingly, the user has greater assurance that a reusable absorbent article 700 will capture all bodily excrement without leakage. The embodiment of FIG. 4 eliminates the need for the mechanical connectors 208a, 208b in the embodiment of FIGS. 1-3, and provides an alternative configuration to decrease the possibility of the absorbent body 600 slipping or moving around within the housing 500, For instance, in FIG. 4, the lining on the medial side of the housing 500 (not shown) may be permanently secured to the housing 500 (e.g., sewn-in) and the absorbent body 600 may be inserted into and removed from the housing 500 via the plurality of flaps 530a, 530b on a lateral side of the housing 500. This allows for the absorbent body 600 to stay in place within the housing 500, without the need for additional mechanical connectors, creating a softer and more comfortable reusable absorbent article 700.

Absorbent body 600 includes many similar features as absorbent body 200 of FIG. 2. In some examples, absorbent body 600 has at least once portion. In some examples, absorbent body has a plurality of portions. The portions of absorbent body 600 may comprise the same materials and absorbency levels as the portions 202, 204, 206 described above with respect to absorbent body 200.

Figure 5:
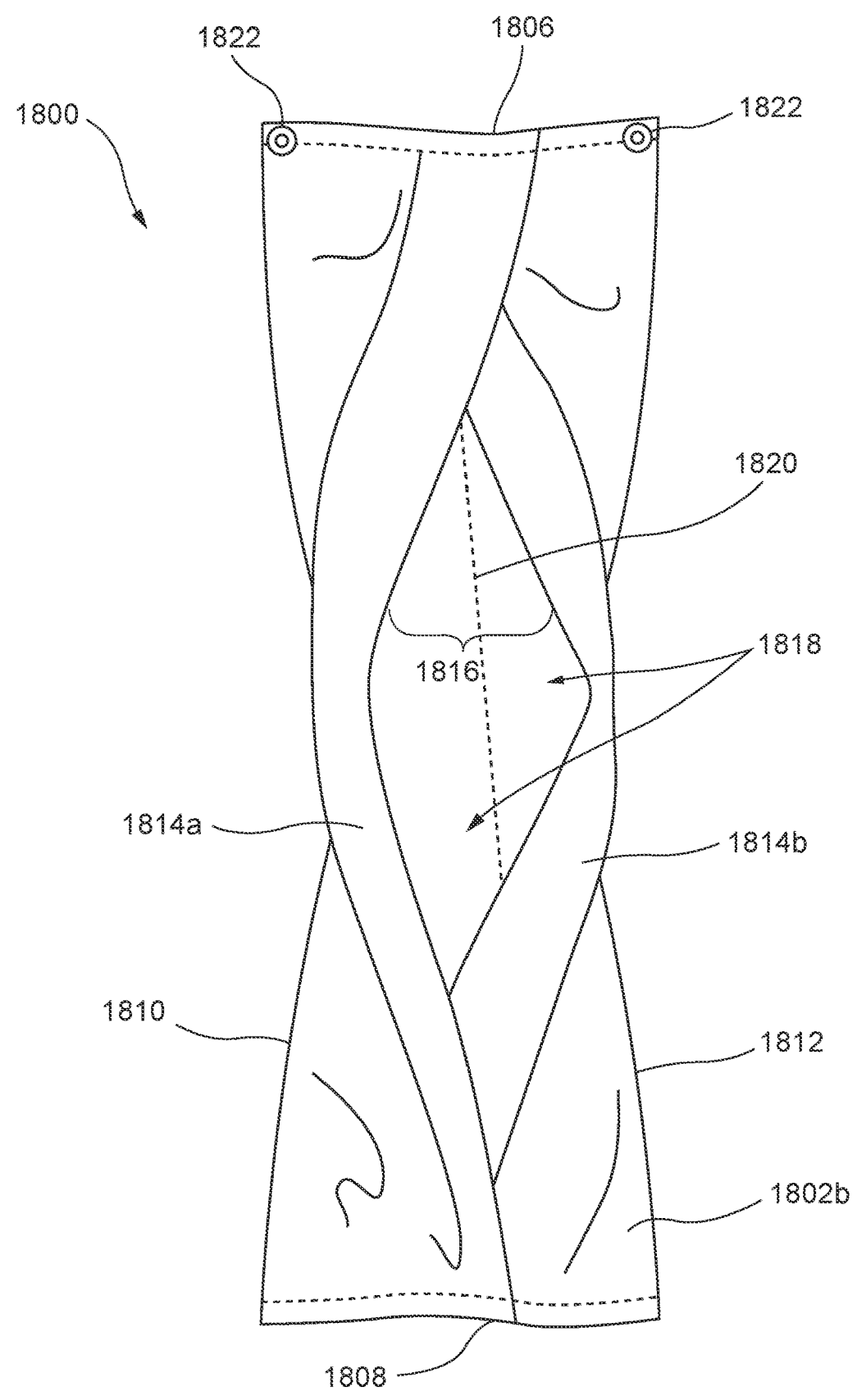
FIG. 5 shows an exemplary partially opened configuration of a reusable absorbent article, according to an embodiment of the present disclosure.
Figure 6:
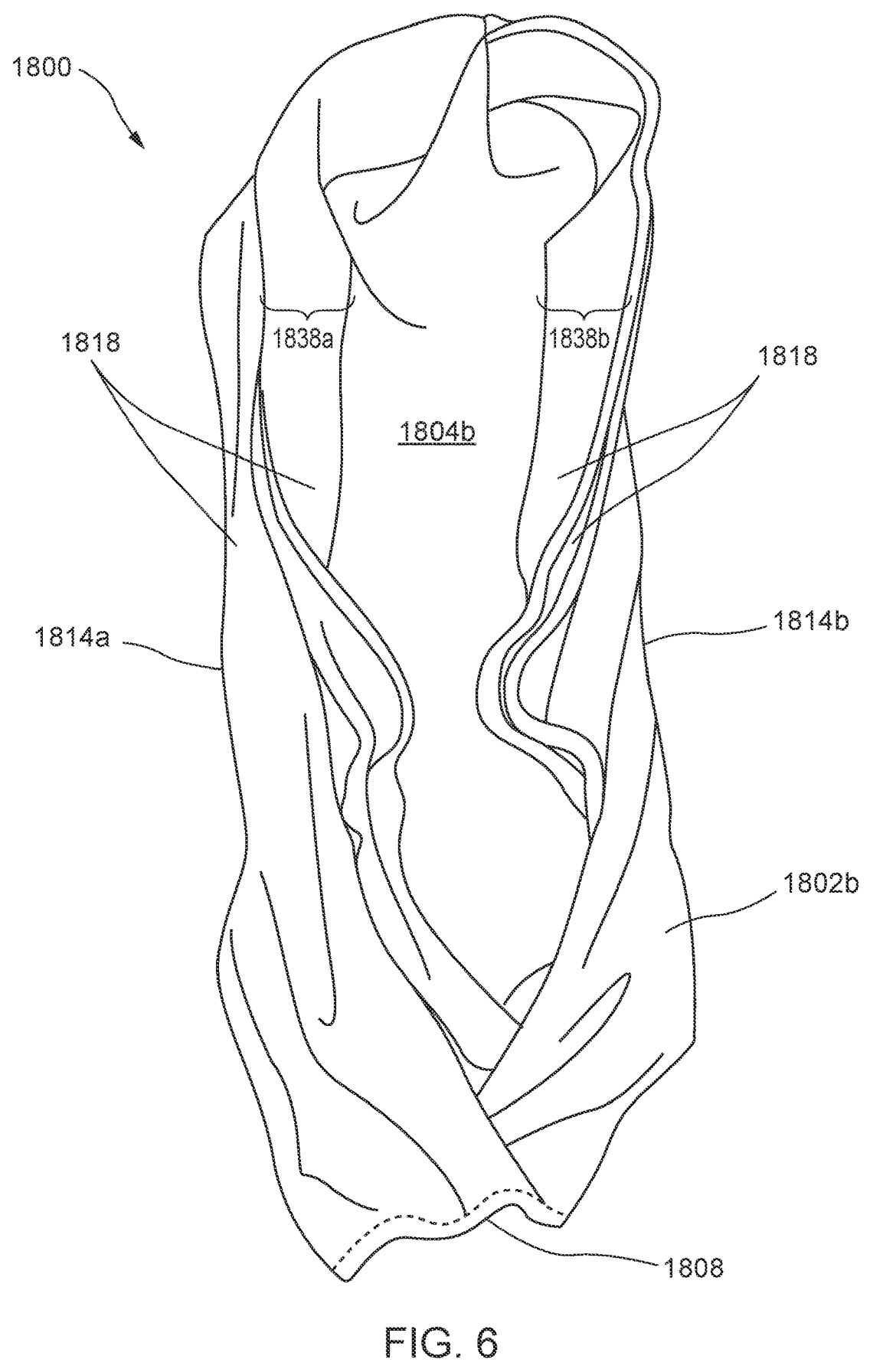

FIGS. 5-6 show a reusable absorbent article 1800, according to another embodiment of the present disclosure. The reusable absorbent article 1800 comprises an outer shell (or housing) 1802 comprising a front panel 1802a (not shown) and a back panel 1802b. FIG. 5 shows a lateral view of the outer shell 1802 (showing the back panel 1802b). The front panel 1802a (not shown) has an outer surface and an inner surface, and has a top edge 1806, a bottom edge 1808, a first side edge 1810, and a second side edge 1812. The outer surface of the front panel 1802a is configured to be worn against the groin of a user. The front panel 1802a may be made of the same material as the material described above regarding portions 202, 204, 206 of FIG. 2. In some embodiments, the front panel 1802a comprises a material configured to inhibit bacterial growth, such as those discussed above with regard to portions 202, 204, 206 of FIG. 2. In some embodiments, the back panel 1802b comprises a plurality of flaps 1814a, 1814b. For example, in some embodiments, a first flap 1814a is coupled to the front panel 1802a along the first side edge 1810 and along at least a portion of the top and bottom edges 1806, 1808. A second flap 1814b is coupled to the front panel 1802a along the second side edge 1812 and along at least a portion of the top and bottom edges 1806, 1808. In some embodiments, the first flap 1814*a* at least partially overlaps with the second flap 1814*b*. In some examples, the overlapping nature of the first and second flaps 1814*a*, 1814*b* reduces liquid or excrement leakage from the shell interior 1816 onto a user's undergarments and/or clothing. In some examples, first and second flaps 1814*a*, 1814*b* comprise a waterproof material to prevent leakage from a medial side (not shown) of the outer shell 1802 to a lateral side (see FIG. 5) of the outer shell 1802. In some embodiments, the first and second flaps 1814*a*, 1814*b* of the back panel 1802*b* comprises a waterproof material, such as those discussed above with regard to housing 100 in FIG. 1. In some examples, the first and second flaps 1814*a*, 1814*b* are coupled and/or sealed by mechanical connectors (not shown), such as hook-and-loop fasteners (e.g., Velcro), male and female connectors, zippers, lip and tape fasteners, double track fasteners, rivets and eyelets, cufflinks, buttons, snaps, clasps, eyelets and laces, adhesives, or safety pins.

As shown in FIG. 5, a shell interior 1816 is formed between the front and back panels 1802*a*, 1802*b* of the outer shell 1802. The shell interior 1816 is accessible by separating and opening the plurality of flaps 1814*a*, 1814*b* of the back panel 1802*b*. A plurality of absorbent layers 1818 are positioned within the shell interior 1816. In some embodiments, each of the plurality of absorbent layers 1818 comprises different levels of absorbency. For instance, each of the plurality of absorbent layers 1818 may comprise an absorbent material, such as those discussed above with regard to portions 202, 204, 206 of FIG. 2. The plurality of absorbent layers 1818 are secured between the front and back panels 1802*a*, 1802*b* along the first and second side edges 1810, 1812 of the front panel 1802*a*. In some embodiments, the plurality of absorbent layers 1818 are sewn in between the front and back panels 1802*a*, 1802*b* along the first and second side edges 1810, 1812 of the front panel 1802*a*. In other embodiments, a mechanical fastener (not shown) is used to secure the plurality of absorbent layers 1818 between the front and back panels 1802*a*, 1802*b*. The plurality of absorbent layers 1818 are cut along a length 1820 to allow for separation of the absorbent layers 1818 and/or to allow for access to the inner surface of the front panel 1802*a*. Each of the plurality of absorbent layers 1818 is cut along a length to form two parts 1838*a*, 1838*b* (shown in FIG. 6). In some embodiments, at least one of the plurality of absorbent layers 1818 is cut along a length 1820 to form two equal parts. In some embodiments, at least one of the plurality of absorbent layers 1818 is cut along a length 1820 to form two unequal parts. In some embodiments, at least one of the plurality of absorbent layers 1818 is cut along a length 1820 to form equal or unequal parts that are different from the parts formed by the cut along a length 1820 of another one of the plurality of absorbent layers 1818, so as to reduce liquid or excrement leakage through the cut lengths of the plurality of absorbent layers 1818. In some embodiments, the cut is non-linear.

The reusable absorbent article 1800 further comprises at least one mechanical connector 1822 configured to secure the reusable absorbent article 1800 to a wearable article (not shown) and to easily remove the reusable absorbent article 1800 when it becomes soiled. In some embodiments, the wearable article is an undergarment or a piece of clothing. For instance, the reusable absorbent article 1800 may be secured to the user's underwear, briefs, thongs, boxers, or directly on a user's pants, trousers, or shorts. In some embodiments, the wearable article may comprise a material such as cotton, cotton blend, satin, muslin, or jersey. In some embodiments, the at least one mechanical connector 1822 comprises a plurality of mechanical connectors. In some non-limiting examples, mechanical connectors 1822 are clasps, snaps, and/or male and female connectors. For instance, in some embodiments, the mechanical connectors 1822 on the reusable absorbent article 1800 are male snap connectors configured to engage with female snap connectors on the wearable article. The mechanical connectors 1822 are not limited by material, and may comprise, for instance, fabric, metal and/or plastic.

The reusable absorbent article 1800 may further comprise at least one of a closed configuration, a partially open configuration, a fully open configuration, and an inside-out configuration.

The reusable absorbent article 1800 is in the closed configuration when the first flap 1814*a* of the back panel 1802*a* of the outer shell 1802 at least partially overlaps with the second flap 1814*b*, substantially enclosing the plurality of absorbent layers 1818 within the shell interior 1816. In other words, when the first flap 1814*a* at least partially overlaps with the second flap 1814*b*, the plurality of absorbent layers 1818 are not visible within the shell interior 1816 from a lateral view of the outer shell 1802, but there may be air flow between the first flap 1814*a* and second flap 1814*b* and into and/or out of the shell interior 1816. In some embodiments, the shape of the reusable absorbent article 1800 in the closed configuration may be a rectangle, an oval, a rounded rectangular share, or an I-shape comprising a middle portion and a plurality of winged portions extending from either side of the middle portion. For instance, the plurality of winged portions may comprise a top winged portion having a first width and a bottom winged portion having a second width. In some embodiments, the second width is different from the first width. For instance, in some embodiments, the second width is larger than the first width. In other embodiments, the first and second widths are equal. In some embodiments, at least one mechanical connector 1822 configured to secure the reusable absorbent article 1800 to a wearable article is positioned on an upper edge of the top winged portion. In some embodiments, the at least one mechanical connector 1822 comprises a plurality of mechanical connectors positioned at distal ends of the upper edge of the top winged portion, as shown in FIG. 5.

The reusable absorbent article 1800 is in the partially open configuration when the first flap 1814*a* and the second flap 1814*b* of the back panel 1802*b* of the outer shell 1802 are separated, such that the plurality of absorbent layers 1818 are exposed within the shell interior 1816. FIG. 5 shows an embodiment of the disclosed reusable absorbent article 1800 in the partially open configuration.

The reusable absorbent article 1800 is in the fully open configuration when the inner surface of the front panel 1802*a* of the outer shell 1802 is exposed within the shell interior 1816 between the first and second flaps 1814*a*, 1814*b* of the back panel 1802*b* of the outer shell 1802 and through the cut along the length 1820 of the plurality of absorbent layers 1818. FIG. 6 shows an embodiment of the disclosed reusable absorbent article 1800 in the fully open configuration.

The reusable absorbent article 1800 is in the inside-out configuration when the first and second flaps 1814*a*, 1814*b* of the back panel 1802*b* of the outer shell 1802 are separated and the plurality of absorbent layers 1818 are folded back to expose the entirety of the inner surface of the front panel 1802*a* of the outer shell 1802.

Therefore, the reusable absorbent article 1800, as shown in FIGS. 5-6, provides unique advantages in that it can be fully opened up and turned inside-out to allow for separation of all of the absorbent layers 1818 and access to the entirety of both the outer surface and inner surface of the front panel 1802*a*. This ultimately allows a user to access and thoroughly clean each of the plurality of absorbent layers 1818 and the front and back panels 1802*a*, 1802*b* of the outer shell 1802, and also allows for shorter drying time when the layers are opened up and separated, allowing for the passage of air over each of the separated layers.

The reusable absorbent article 1800 may also include a raised lip portion (not shown) around the perimeter of the outer shell 1802. For example, the lip portion is a narrow section of fabric extending over the edges of the front panel 1802*a* and back panel 1802*b*. In some examples, the lip portion is a seam configured to secured the front panel 1802*a* to the back panel 1802*b*. In some embodiments, the lip portion comprises a waterproof or moisture-wicking material. Therefore, the lip portion may provide spill and leak protection for liquid received on the outer surface of the front panel 1802*a*. For example, when the reusable absorbent article 1800 is worn by a user and receives bodily fluids, the fluid does not leak onto the user's undergarments, because the liquid is caught by the lip portion. In some embodiments of the present disclosure, the reusable absorbent article does not include a lip portion.

In some embodiments (shown in FIG. 7), the front panel 1802*a* comprises a plurality of flaps 1840*a*, 1840*b* configured in the same manner as that of the first and second flaps 1814*a*, 1814*b*, as described above, wherein the plurality of flaps 1840*a*, 1840*b* comprise a material configured to inhibit bacterial growth, such as those discussed above with regard to portions 202, 204, 206 of FIG. 2. In such embodiments, the back panel 1802*b* may comprise a single contiguous panel (rather than first and second flaps 1814*a*, 1814*b*), wherein the back panel 1802*b* comprises a waterproof material, such as those discussed above with regard to housing 100 in FIG. 1. In such embodiments, the front panel 1802*a* may further comprise a pair of wings 1850*a*, 1850*b*, wherein the pair of wings 1850*a*, 1850*b* comprises at least one mechanical connector 1852*a*, 1852*b* configured to secure the reusable absorbent article 1800 to a wearable article. In some non-limiting examples, the at least one mechanical connector 1852*a*, 1852*b* is a clasp, snap, and/or male and female connector, configured to engage with the at least one mechanical connector on the other wing. For instance, in some embodiments, the at least one mechanical connector 1852*a* on one wing 1850*a* is a female snap connector configured to engage with a male snap connector 1852*b* on the other wing 1850*b*, to secure the pair of wings 1850*a*, 1850*b* together around a groin portion of a wearable article (in a manner similar to wings 102*a*, 102*b* of housing 100 in FIG. 1). In such embodiments, the back panel 1802*b* may further comprise at least one fastener 1854*a-c* configured to secure the reusable absorbent article 1800 to a wearable article. In some examples, the at least one fastener 1854*a-c* comprises a hook-and-loop fastener. In such embodiments, at least one absorbent layer 1858 is secured between the front and back panels 1802*a*, 1802*b*.

Figure 7:
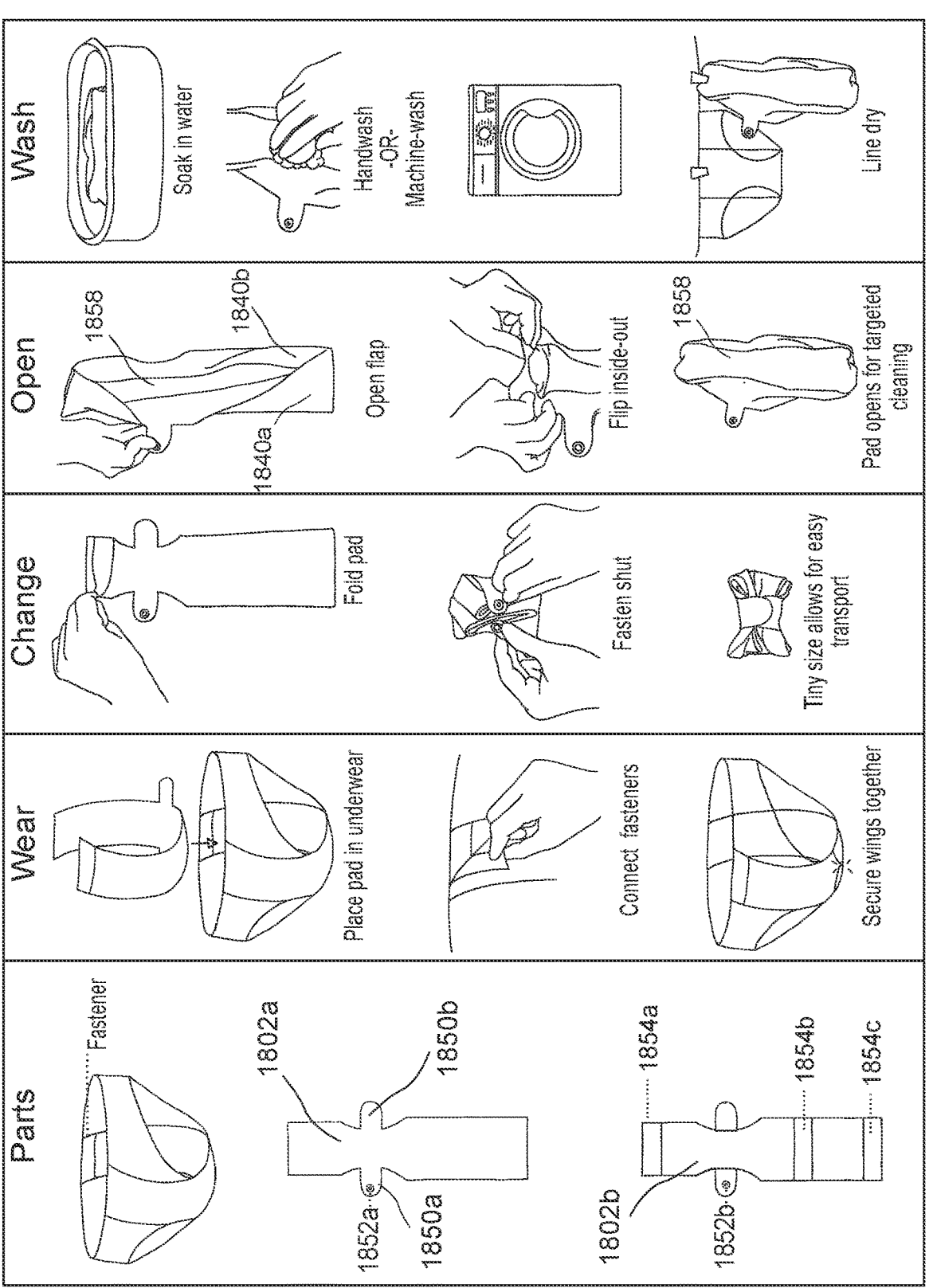
FIG. 7 shows exemplary use and cleaning procedures for a reusable absorbent article and wearable article, according to an embodiment of the present disclosure.

Therefore, the reusable absorbent article 1800 as shown in FIG. 7 provides similar advantages as the embodiment shown in FIGS. 5-6 in that it can be fully opened up and turned inside-out to allow for separation of all of the absorbent layers 1858 and access to the various surfaces of the front and back panels 1802*a*, 1802*b*. The opening is along one side of the reusable absorbent article 1800 which improves the user's comfort while still allowing a user to access and thoroughly clean each of the absorbent layers 1858 and the front and back panels 1802*a*, 1802*b* of the outer shell 1802, and also allows for shorter drying time when the layers are opened up and separated, allowing for the passage of air over each of the separated layers. The absorbent layer(s) and waterproof layer(s) are attached to each other on the side opposite the opening.

FIG. 7 also provides exemplary use and cleaning procedures for the reusable absorbent article 1800.

In some embodiments, the wearable article is an undergarment or a piece of clothing. For instance, in a non-limiting example, the wearable article may be underwear, briefs, thongs, boxers, pants, trousers, or shorts. In some embodiments, the wearable article comprises a waistband portion positioned at a user's waist and a groin portion configured to be worn adjacent to the user's groin area. In some embodiments, the wearable article further comprises at least one attachment mechanism for securing the reusable absorbent article 1800 to the wearable article. For instance, a plurality of mechanical connectors configured to secure the reusable absorbent article 1800 to the wearable article may be positioned on the wearable article. In some embodiments, the plurality of mechanical connectors are positioned on an inner surface of the wearable article. In some non-limiting examples, the plurality of mechanical connectors are clasps, snaps, and/or male and female connectors, configured to engage with the mechanical connectors 1822 on the reusable absorbent article 1800. For instance, in some embodiments, the mechanical connectors on the wearable article are female snap connectors configured to engage with male snap connectors on the reusable absorbent article 1800. In some embodiments, the mechanical connectors on the wearable article are hook and loop connectors configured to engage with the hook and loop connectors on the reusable absorbent article 1800.

According to an embodiment of the present disclosure, the at least one attachment mechanism on the wearable article comprises a band having first and second ends secured to the inner surface. In some embodiments, the band is secured to the inner surface of the wearable article between the waistband portion and the groin portion. The band is configured to receive an end portion of the reusable absorbent article 1800, such that the end portion of the reusable absorbent article 1800 can be positioned underneath the band to accommodate repositioning by the user. Thus, while the reusable absorbent article 1800 is secured to an inside surface of the front of the wearable article through mechanical connectors, the end portion of the reusable absorbent article can slide underneath the band in a vertical direction. Therefore, the band holds the end portion of the reusable absorbent article 1800 in place, while allowing for vertical flexibility and movement of the reusable absorbent article 1800 to accommodate the user's movement (i.e., when the user moves from a standing position to a sitting position, or vice versa). Accordingly, the user has greater assurance that a reusable absorbent article 1800 will capture all bodily excrement without leakage and provide greater coverage to protect the wearable article from staining. The band also eliminates the need for bulky or uncomfortable mechanical connectors in the back of the wearable article, providing greater comfort to the user. In some embodiments, the band comprises a flexible or elastic material. In some embodiments, the band may be formed integrally with the wearable article. In some embodiments, the band may be a separate piece secured to an inner surface of the wearable article.

According to the present disclosure, in some embodiments, an absorbent undergarment kit comprises a wearable article or undergarment configured to be worn against the groin of a user, at least one reusable absorbent article 1800, and a plurality of mechanical connectors configured to secure the reusable absorbent article to the undergarment. In other embodiments, a wearable article for providing absorbent relief comprises an undergarment configured to be worn against the groin of a user, a reusable absorbent article 1800, and at least one attachment mechanism securing the reusable absorbent article 1800 to the undergarment.

Therefore, the reusable absorbent articles of the present disclosure provide for more thorough cleaning and faster drying than conventional products. In some examples, the disclosed absorbent body stays in place without using mechanical connectors; this provides added comfort for a user. In some examples, the disclosed absorbent body uses one or more points of contact to remain in place in a user's undergarment. In some examples, a size of the absorbent body, housing, and/or reusable absorbent article provides full coverage insert to accommodate all types of bodily excretion, including various types of menstruation (front-bleeding, back-bleeding, heavy-bleeding, etc.).

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

What is claimed is:

1. A reusable absorbent article, comprising:

a) an outer shell, wherein the outer shell comprises:

i) a front panel; and ii) a back panel comprising a waterproof material, wherein the front panel is coupled to the back panel along a first side edge and at least a portion of top and bottom edges, and wherein a shell interior is formed between the front and back panels of the outer shell;

b) at least one absorbent layer positioned within the shell interior; and c) at least one mechanical connector configured to secure the reusable absorbent article to a wearable article, wherein said front panel, said back panel and said at least one absorbent layer can be partially separated from each other, wherein the reusable absorbent article is configured to have a closed configuration, a partially open configuration, and a fully open configuration; and wherein at least part of the at least one absorbent layer is permanently secured to the outer shell.

2. The reusable absorbent article of claim 1, wherein said waterproof material is selected from the group consisting of nylon, polyester, vinyl, coated materials and laminates.

3. The reusable absorbent article of claim 2, wherein said coated materials comprise a waterproofing material selected from the group consisting of rubber, polyvinyl chloride, polyurethane, silicone elastomer, fluoropolymers and wax.

4. A reusable absorbent article, comprising:

a) an outer shell, wherein the outer shell comprises:

i) a front panel having an outer surface and an inner surface, and having a top edge, a bottom edge, a first side edge, and a second side edge; and ii) a back panel comprising a first flap and a second flap, wherein the first flap of the back panel is coupled to the front panel along the first side edge and at least a portion of the top and bottom edges, and wherein the second flap of the back panel is coupled to the front panel along the second side edge and at least a portion of the top and bottom edges, and wherein the first flap of the back panel at least partially overlaps with the second flap of the back panel;

wherein a shell interior is formed between the front and back panels of the outer shell;

b) a plurality of absorbent layers positioned within the shell interior, wherein said absorbent layers are secured between the front and back panels along the first and second side edges of the front panel, wherein the plurality of absorbent layers are cut and/or unattached along a length to allow separation of the absorbent layers; and c) at least one mechanical connector configured to secure the reusable absorbent article to an undergarment, wherein the reusable absorbent article comprises a closed configuration, a partially open configuration, a fully open configuration, and an inside-out configuration, and wherein the back panel of the outer shell comprises a waterproof material.

5. The reusable absorbent article of claim 4, wherein the reusable absorbent article is in the closed configuration when the first flap of the back panel of the outer shell overlaps with the second flap, substantially enclosing the plurality of absorbent layers within the shell interior.

6. The reusable absorbent article of claim 4, wherein the reusable absorbent article is in the partially open configuration when the plurality of absorbent layers are exposed within the shell interior between the first and second flaps of the back panel of the outer shell.

7. The reusable absorbent article of claim 4, wherein the reusable absorbent article is in the fully open configuration when the inner surface of the front panel of the outer shell is exposed within the shell interior between the first and second flaps of the back panel of the outer shell and through a cut along the length of the plurality of absorbent layers.

8. The reusable absorbent article of claim 4, wherein the reusable absorbent article is in the inside-out configuration when the first and second flaps of the back panel of the outer shell are separated and the plurality of absorbent layers are folded back to expose the entirety of the inner surface of the front panel of the outer shell.

9. The reusable absorbent article of claim 4, wherein each of the plurality of absorbent layers comprises a level of absorbance different from that of each other absorbent layer.

10. The reusable absorbent article of claim 4, wherein the front panel of the outer shell comprises an antimicrobial material.

11. The reusable absorbent article of claim 4, wherein the shape of the reusable absorbent article in the closed configuration is selected from the group consisting of a rectangle, an oval, a rounded rectangular shape, and an I-shape comprising a middle portion and a plurality of winged portions extending from either side of the middle portion.

12. The reusable absorbent article of claim 11, wherein the plurality of winged portions comprises a top winged portion having a first width and a bottom winged portion having a second width, and wherein the second width is larger than the first width.

13. The reusable absorbent article of claim 12, wherein the at least one mechanical connector comprises a plurality of mechanical connectors positioned on an upper edge of the top winged portion.

14. The reusable absorbent article of claim 4, wherein said waterproof material is selected from the group consisting of nylon, polyester, vinyl, coated materials and laminates.

15. The reusable absorbent article of claim 14, wherein said coated materials comprise a waterproofing material selected from the group consisting of rubber, polyvinyl chloride, polyurethane, silicone elastomer, fluoropolymers and wax.

16. A wearable article for providing absorbent relief, comprising:

a) an undergarment configured to be worn against the groin of a user, wherein said undergarment comprises a waistband portion and a groin portion; and b) a reusable absorbent article according to claim 4.

17. The wearable article of claim 16, wherein the front panel comprises a pair of wings, wherein the at least one mechanical connector is located on the pair of wings.

18. The wearable article of claim 16, wherein the back panel comprises at least one mechanical connector.

19. An absorbent undergarment kit, comprising:

a) an undergarment configured to be worn against the groin of a user, wherein said undergarment comprises a waistband portion and a groin portion;

b) at least one reusable absorbent article, comprising:

1) an outer shell, wherein the outer shell comprises:

i) a front panel having an outer surface and an inner surface, and having a top edge, a bottom edge, a first side edge, and a second side edge; and ii) a back panel comprising a first flap and a second flap, wherein the first flap of the back panel is coupled to the front panel along the first side edge and a least a portion of the top and bottom edges, and wherein the second flap of the back panel is coupled to the front panel along the second side edge and at least a portion of the top and bottom edges, and wherein the first flap at least partially overlaps with the second flap; wherein a shell interior is created between the front and back panels of the outer shell; and 2) a plurality of absorbent layers positioned within the shell interior and secured between the front and back panels along the first and second side edges of the front panel, and wherein the plurality of absorbent layers are cut along a length; and wherein the reusable absorbent article comprises a closed configuration, a partially open configuration, a fully open configuration, and an inside-out configuration; and c) a plurality of mechanical connectors configured to secure the reusable absorbent article to the undergarment;

wherein the back panel of the outer shell comprises a waterproof material.

20. The absorbent undergarment kit of claim 19, wherein the plurality of mechanical connectors are positioned on an inner surface of the undergarment between said waistband portion and said groin portion of the undergarment.

\* \* \* \* \*